(12) United States Patent
Helfand et al.

(10) Patent No.: US 7,223,596 B2
(45) Date of Patent: May 29, 2007

(54) MALIGNANT ENDOTHELIAL CELL LINE AND USES THEREOF IN MODELS FOR ANGIOGENESIS

(75) Inventors: Stuart Charles Helfand, Madison, WI (US); Nasim Akhtar, Madison, WI (US); Erin Beth Dickerson, Madison, WI (US); Marcia Lillian Padilla, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 455 days.

(21) Appl. No.: 10/655,727

(22) Filed: Sep. 5, 2003

(65) Prior Publication Data

US 2005/0054089 A1 Mar. 10, 2005

(51) Int. Cl.
*C12N 5/10* (2006.01)
*C12N 5/06* (2006.01)
*C12N 5/02* (2006.01)

(52) U.S. Cl. ..................... 435/350; 435/325; 424/93.7; 424/93.1

(58) Field of Classification Search ............... 424/93.1, 424/93.7; 435/325
See application file for complete search history.

(56) References Cited

OTHER PUBLICATIONS

Smith, "Hemangiosarcoma in dogs and cats", Vet Clin North Am Small Animal Pract, May 2003, 33(3):533-52, vi, abstract.*
Yamagami et al., "Hepatic lymphangiomatosis in a young dog", J Vet Med Sci, Aug. 2002, 64(8):743-5, abstract.*
Pan et al., "Expression of endothelial cell Igg Fc receptors and markers on various cultures", Chin Med J (Engl), Feb. 1999, 112(2):157-61, abstract.*
Shimura et al., "Brain tumor induced in dogs by intracerebral inoculation of SR-RSV induced cultured tumor cells-electron microscopic study", No Shinkei Geka, May 1985, 13(5):521-8, abstract.*
Bhattacharya et al., "Dual signaling by the $\alpha_v\beta_3$—integrin activates cytosolic $PLA_2$ in bovine pulmonary artery endothelial cells", Am. J. Physiol. Lung Cell Mol. Physiol. 2001 280:L1049-L1056.
Bouïs et al., "Endothelium in vitro:A review of human vascular endothelial cell lines for blood vessel-related research", Angiogenesis 2001 4:91-102.
Cheresh, David A., "Human endothelial cells synthesize and express an Arg-Gly-Asp-directed adhesion receptor involved in attachment to fibrinogen and von Willebrand factor", Proc. Natl. Acad. Sci. USA 1987 84:6471-6475.
Fox et al., "Arteriolar Flow Recruitment with Vitronectin Receptor Stimulation Linked to Remote Wall Shear Stress", Microvascular Research 2002 64:414-424.
Frame et al., "Localized Adenovirus-Mediated Gene Transfer Into Vascular Smooth Muscle in the Hamster Cheek Pouch", Microcirculation 2001 8:403-413.
Gumkowski et al., "Heterogeneity of Mouse Vascular Endothelium", Blood Vessels 1987 24:11-23.
Illera et al., "A Role for $\alpha_v\beta_3$ Integrin During Implantation in the Rabbit Model", Biology of Reproduction 2003 68:766-771.
Jarrell et al., "Human adult endothelial cell growth in culture", J. Vasc. Surg. 1984 1:757-764.
Kemmner et al., "A rapid and simple procedure for dissociation of tumor tissue from the human colon", J. Cancer Res. Clin. Oncol. 1987 113:400-401.
Koenig et al., "Expression and Significance of p53, Rb, p21/*waf*-1, p16/*ink-4a*, and PTEN Tumor Suppressors in Canine Melanoma", Vet Pathol 2002 39:458-472.
Kumar et al., "Heterogeneity in endothelial cells from large vessels and microvessels", Differentiation 1987 36:57-70.
Leven et al., "Extracellular Matrix Stimulation of Guinea Pig Megakaryocyte Proplatelet Formation in vitro Is Mediated Through the Vitronectin Receptor", Exp. Hematol. 1992 20:1316-1322.
Miyauchi et al., "Recognition of Osteopontin and Related Peptides by an $\alpha_v\beta_3$ Integrin Stimulates Immediate Cell Signals in Osteoclasts", The Journal of Biological Chemistry 1991 266(30):20369-20374.
Muthukkaruppan et al., "Angiogenesis in the Mouse Cornea", Science 1979 205(4413):1416-1418.
Obeso et al., "Methods in Laboratory Investigation—A Hemangioendothelioma-Derived Cell Line:Its Use as a Model for the Study of Endothelial Cell Biology", Laboratory Investigation 1990 63(2):259-269.
Ritt et al., "Sustained nuclear localization of p21/WAF-1 upon growth arrest induced by contact inhibition", Cancer Letters 2000 158:73-84.
Sipkins et al., "Detection of tumor angiogenesis in vivo by $\alpha_v\beta_3$—targeted magnetic resonance imaging", Nature Medicine 1998 4(5):623-626.
Solovey et al., "Circulating Activated Endothelial Cells in Sickle Cell Anemia", The New England Journal of Medicine 1997 1584-1590.

* cited by examiner

*Primary Examiner*—Ruth A Davis
(74) *Attorney, Agent, or Firm*—Licata & Tyrrell P.C.

(57) ABSTRACT

An immortalized hemangiosarcoma cell line of malignant canine endothelial cells which possesses surface expression characteristics and growth factor and cytokine expression profiles typical of nonmalignant activated endothelial cells is provided. In vitro and in vivo models for angiogenesis produced from this cell line as well as methods for identifying antiangiogenic agents using these models are also provided.

4 Claims, No Drawings

SEQUENCE LISTING

<160> NUMBER OF SEQ ID NOS: 20

<210> SEQ ID NO 1
<211> LENGTH: 22
<212> TYPE: DNA
<213> ORGANISM: Artificial sequence
<220> FEATURE:
<223> OTHER INFORMATION: Synthetic

```
<400> SEQUENCE: 1
ccatgaactt tctgctctct tg                                          22

<210> SEQ ID NO 2
<211> LENGTH: 21
<212> TYPE: DNA
<213> ORGANISM: Artificial sequence
<220> FEATURE:
<223> OTHER INFORMATION: Synthetic

<400> SEQUENCE: 2
ttgtcttgct ctatctttct t                                           21

<210> SEQ ID NO 3
<211> LENGTH: 24
<212> TYPE: DNA
<213> ORGANISM: Artificial sequence
<220> FEATURE:
<223> OTHER INFORMATION: Synthetic

<400> SEQUENCE: 3
aagcagccca ttcatggtct ttgc                                        24

<210> SEQ ID NO 4
<211> LENGTH: 23
<212> TYPE: DNA
<213> ORGANISM: Artificial sequence
<220> FEATURE:
<223> OTHER INFORMATION: Synthetic

<400> SEQUENCE: 4
ccatcaggga tcagggtatc aag                                         23

<210> SEQ ID NO 5
<211> LENGTH: 24
<212> TYPE: DNA
<213> ORGANISM: Artificial sequence
<220> FEATURE:
<223> OTHER INFORMATION: Synthetic

<400> SEQUENCE: 5
actggagcct acaagtgctt ctay                                        24

<210> SEQ ID NO 6
<211> LENGTH: 23
<212> TYPE: DNA
<213> ORGANISM: Artificial sequence
<220> FEATURE:
<223> OTHER INFORMATION: Synthetic

<400> SEQUENCE: 6
tyttcttggt catcagycca ctg                                         23

<210> SEQ ID NO 7
<211> LENGTH: 19
<212> TYPE: DNA
<213> ORGANISM: Artificial sequence
<220> FEATURE:
<223> OTHER INFORMATION: Synthetic

<400> SEQUENCE: 7
cttcaaggac cccagcggc                                              19

<210> SEQ ID NO 8
<211> LENGTH: 17
```

```
<212> TYPE: DNA
<213> ORGANISM: Artificial sequence
<220> FEATURE:
<223> OTHER INFORMATION: Synthetic

<400> SEQUENCE: 8
gctcttagca gacttgg                                                      17

<210> SEQ ID NO 9
<211> LENGTH: 18
<212> TYPE: DNA
<213> ORGANISM: Artificial sequence
<220> FEATURE:
<223> OTHER INFORMATION: Synthetic

<400> SEQUENCE: 9
tcagaacttc gatgccag                                                     18

<210> SEQ ID NO 10
<211> LENGTH: 20
<212> TYPE: DNA
<213> ORGANISM: Artificial sequence
<220> FEATURE:
<223> OTHER INFORMATION: Synthetic

<400> SEQUENCE: 10
tttcacggat cttgtttctc                                                   20

<210> SEQ ID NO 11
<211> LENGTH: 20
<212> TYPE: DNA
<213> ORGANISM: Artificial sequence
<220> FEATURE:
<223> OTHER INFORMATION: Synthetic

<400> SEQUENCE: 11
ccgtatgaga tcaagcagat                                                   20

<210> SEQ ID NO 12
<211> LENGTH: 21
<212> TYPE: DNA
<213> ORGANISM: Artificial sequence
<220> FEATURE:
<223> OTHER INFORMATION: Synthetic

<400> SEQUENCE: 12
ttacgggtcc tcaatatcga g                                                 21

<210> SEQ ID NO 13
<211> LENGTH: 18
<212> TYPE: DNA
<213> ORGANISM: Artificial sequence
<220> FEATURE:
<223> OTHER INFORMATION: Synthetic

<400> SEQUENCE: 13
atctgtatga ggaagact                                                     18

<210> SEQ ID NO 14
<211> LENGTH: 18
<212> TYPE: DNA
<213> ORGANISM: Artificial sequence
<220> FEATURE:
<223> OTHER INFORMATION: Synthetic

<400> SEQUENCE: 14
```

```
gaccagaagg tccatcaa                                                        18

<210> SEQ ID NO 15
<211> LENGTH: 22
<212> TYPE: DNA
<213> ORGANISM: Artificial sequence
<220> FEATURE:
<223> OTHER INFORMATION: Synthetic

<400> SEQUENCE: 15
ccagagtcag tgtcacaaaa cc                                                   22

<210> SEQ ID NO 16
<211> LENGTH: 21
<212> TYPE: DNA
<213> ORGANISM: Artificial sequence
<220> FEATURE:
<223> OTHER INFORMATION: Synthetic

<400> SEQUENCE: 16
cttcttccag tataaggctc c                                                    21

<210> SEQ ID NO 17
<211> LENGTH: 24
<212> TYPE: DNA
<213> ORGANISM: Artificial sequence
<220> FEATURE:
<223> OTHER INFORMATION: Synthetic

<400> SEQUENCE: 17
caccctggtc attacagaat attg                                                 24

<210> SEQ ID NO 18
<211> LENGTH: 24
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (15)..(15)
<223> OTHER INFORMATION: n=a, c, g or t

<400> SEQUENCE: 18
cggaagcctt ccttnatcat cttg                                                 24

<210> SEQ ID NO 19
<211> LENGTH: 24
<212> TYPE: DNA
<213> ORGANISM: Artificial sequence
<220> FEATURE:
<223> OTHER INFORMATION: Synthetic

<400> SEQUENCE: 19
catgtttgag acattcaaca cccc                                                 24

<210> SEQ ID NO 20
<211> LENGTH: 23
<212> TYPE: DNA
<213> ORGANISM: Artificial sequence
<220> FEATURE:
<223> OTHER INFORMATION: Synthetic

<400> SEQUENCE: 20
gccatctctt gctcgaagtc cag                                                  23
```

MALIGNANT ENDOTHELIAL CELL LINE AND USES THEREOF IN MODELS FOR ANGIOGENESIS

This invention was made with United State government support awarded by the following agencies:

NIH CA86264.

The United States has certain rights in this invention.

FIELD OF THE INVENTION

A malignant endothelial cell line developed from a canine hemangiosarcoma that induces endothelial cell tumors in immunocompromised mice is provided. Suppression of growth of these cells, as well as growth of tumors in immunocompromised mouse injected with these cells, are viewed as antiangiogenic responses. Accordingly, these cells and mice or other immunocompromised nonhuman mammals injected with these cells provide models for angiogenesis. Agents identified as suppressing cell growth in culture or tumor growth in these animal models are expected to be useful as antiangiogenic agents. Such agents are useful in the treatment of cancer as well as other diseases mediated by uncontrolled angiogenesis.

BACKGROUND OF THE INVENTION

Angiogenesis, the formation of new blood vessels, has been intensively studied over the past several decades because of its fundamental importance in tissue development, vascular diseases, and cancer. Angiogenesis is most active during fetal development. After birth angiogenesis is an important physiological function in the ovary, placenta, and in wound healing.

Pathological angiogenesis, that is inappropriate and unregulated, is a prominent feature of malignancy that facilitates tumor growth and metastasis. Improved treatments of malignancies that have progressed to the proangiogenic phenotype require relevant models to test the safety and efficacy of innovative antiangiogenic therapies.

There are a number of methods available for identifying potential antiangiogenic agents. One of these involves examining the effects of an agent on blood vessel formation in the eye in an intact mouse.

However, systems to study angiogenesis in the laboratory are limited by the transient nature of angiogenic events and limited accessibility to angiogenic tissues. Sources of endothelial cells currently used in the laboratory include human umbilical vein, and bovine aorta, pulmonary vein, and pulmonary artery (Jarrell et al. J. Vasc. Surg. 1984 1:757–764; Simonescu, N. and Simonescu, M. (eds) Endothelial Cell Biology in Health and Disease. New York: Plenum Press, 1988; Thilo-Korner, D. and Freshmey, R. I. (eds) In the Endothelial Cell—A Pluripotent Control Cell of the Vessel Wall. Basel:Karger, 1983). A malignant hemangioendothelioma of murine origin is also used for studying endothelial cell biology (Obeso et al. Lab. Invest. 1990 63:259–269). Other endothelial cells, such as those derived from bovine adrenal cortex or retina, rat brain, and mouse aorta, epididymal fat pad, thoracic duct, or liver have been more difficult to maintain in stable long term culture (Gumkowski et al. Blood Vessels 1987 24:11–23; Jaffe, E. A. (ed.) The Biology of Endothelial Cells. The Hague: Martinus Nijhoff, 1983; Kumar et al. Differentiation 1987 36:57–70).

SUMMARY OF THE INVENTION

An aspect of the present invention relates to a malignant endothelial cell line derived from a canine hemangiosarcoma possessing surface expression characteristics and growth factor and cytokine expression profiles typical of nonmalignant activated endothelial cells.

Another aspect of the present invention relates to an endothelial cell model for angiogenesis comprising this malignant endothelial cell line.

Another aspect of the present invention relates to a method for identifying antiangiogenic agents which comprises assessing growth of cells in the endothelial cell model in the presence and absence of a test agent. The ability of a test agent to decrease growth of the cells as compared to cell growth in the absence of the test agent is indicative of the test agent being an antiangiogenic agent.

Another aspect of the present invention relates to a nonhuman animal model for angiogenesis comprising an immunocompromised nonhuman mammal, preferably a rodent such as a mouse or rat, which develops canine endothelial cell tumors. In this model, the nonhuman mammal is injected with cells of the malignant endothelial cell line derived from a canine hemangiosarcoma.

Another aspect of the present invention relates to a method for identifying antiangiogenic agents that comprises administering to an immunocompromised nonhuman mammal, preferably an immunocompromised rodent, more preferably an immunocompromised mouse, which develops canine endothelial cell tumors a test agent and assessing the ability of the test agent to suppress growth of endothelial cell tumors in the immunocompromised nonhuman mammal. The ability of a test agent to suppress growth of canine endothelial cell tumors in the immunocompromised nonhuman mammal is indicative of an antiangiogenic response. Such agents are expected to be useful in the treatment of cancer and other diseases mediated by uncontrolled angiogenesis.

DETAILED DESCRIPTION OF THE INVENTION

Neoplastic cells have been used to study the developmental processes and functions of normal cells because tumor cells are capable of proliferating both in vitro and in vivo while at the same time maintaining many of the properties of their normal counterparts. For example, plasmacytomas have provided material that has led to the characterization of Ig structure. In addition, studies of teratomas have helped to clarify how differentiation takes place (Obeso et al. Lab. Invest. 1990 63:259–269). In the same way endothelial cells derived from tumors or endothelial call tumors can be used to understand the biology of endothelial cells.

In the present invention, a malignant endothelial cell line derived from hemangiosarcoma cells of a spontaneous subcutaneous tumor in a dog is provided. This immortalized cell line was obtained by transplanting a portion of the spontaneous subcutaneous tumor into a mouse and then isolating an immortalized cell line after this mouse passage. The immortalized cells of this cell line are referred to herein as SB-HSA cells or SB-HSA tumor cells. Dissociated SB-HSA tumor cells obtained from the primary canine hemangiosarcoma tumor explant in a NOD-SCID mouse were examined via flow cytometry. The dissociated tumor cells showed bright staining with an anti-CD146 antibody and an anti-$\alpha_v\beta_3$ integrin antibody that does not bind to $\alpha_v\beta_3$ integrin in the mouse. CD146 is expressed chiefly by endothelial cells and platelets while $\alpha_v\beta_3$ integrin is an adhesion molecule found on mitotically active endothelial cells. Accordingly, the staining pattern exhibited by the cells derived from the primary tumor explant is indicative of an endothelial, non-murine cell type consistent with the canine hemangiosarcoma transplanted into the first mouse.

Immunohistochemical staining of SB-HSA tumor cells obtained from the primary canine hemangiosarcoma tumor explant in NOD-SCID mice exhibited positive staining for CD146, PECAM-1 and Factor VIII, as well, thus confirming the endothelial nature of the mouse tumor.

Using reverse transcriptase-polymerase chain reaction (RT-PCR), the expression of message of several endothelial cell growth factors, receptor tyrosine kinases and matrix metalloproteinases (MMPs) in SB-HSA tumor cells was assessed. Using primers designed from canine gene sequences, SB-HSA cells were found to express message for proangiogenic proteins including VEGF, basic fibroblast growth factor (bFGF), and interleukin (IL)-8 that are stimulatory to endothelial cell growth. Message for receptor tyrosine kinase VEGFR-1 and -2 and c-kit were also expressed as was message for stem cell factor (SCF), the ligand for c-kit. In addition, SB-HSA cells expressed message for MMP-2 and MMP-13. Taken together, these results are indicative of SB-HSA cells expressing proteins and receptors that stimulate endothelial cell growth. Accordingly these cells have the potential to promote their own growth in an autocrine and paracrine manner. In addition, MMP expression is indicative of the cells' capability of expansion through the extracellular matrix.

The immortalized cell line of SB-HSA cells has been deposited with the American Type Culture Collection (Manassas, Va.), an International Depository Authority, under the provisions of the Budapest Treaty on Jun. 10, 2004 and has been assigned ATTC Deposit Number PTA-6071. All restrictions upon public access to this cell line will be irrevocably removed upon granting of this patent application. The Deposit will be maintained in a public depository for a period of thirty years after the date of deposit or five years after the last request for a sample or for the enforceable life of the patent, whichever is longer. The above-referenced cell line was viable at the time of the deposit. The Deposit will be replaced if viable samples cannot be dispensed by the depository.

Use of a renewable source of endothelial cells such as the cell line of the present invention in studies is advantageous since primary endothelial cells have a limited lifespan and display characteristics that differ from batch to batch due to their multidonor origin (Bouis et al. Angiogenesis 2001 4:91–102). The immortalized cell line of the present invention provides a constant source of cells thereby decreasing variability in assays using these cells.

The cell line of the present invention is useful as an endothelial cell model for studying angiogenesis as well as for investigation of strategies to modulate angiogenesis in cancer and other diseases mediated by uncontrolled angiogenesis. Inhibition of SB-HSA cell growth in culture by a test agent is indicative of the test agent possessing antiangiogenic activity.

Accordingly, another aspect of the present invention relates to an endothelial cell model for angiogenesis which comprises SB-HSA cells of the immortalized cell line of the present invention. The endothelial cell model is useful in identifying agents possessing antiangiogenic activity. In this method, cultures comprising the cell line of the present invention are contacted with a test agent. For purposes of the present invention, by "contact" or "contacted" or "contacting" it is meant that the test agent is added to the culture media of the cells. Growth of the cells in culture in the presence of the test agent is compared with growth of the cells in culture in the absence of the test agent. A decrease in growth of the cells in the presence of the test agent as compared to cell growth in the absence of the test agent is indicative of the test agent being an antiangiogenic agent.

Unlike cells isolated from the primary tumor, the immortalized cell line of the present invention is capable of causing tumors when injected into immunocompromised nonhuman mammals, preferably immunocompromised rodents, more preferably immunocompromised mice or rats.

For example, cohorts of NOD-SCID mice injected with SB-HSA cells over their dorsum typically developed large subcutaneous tumors by three to four weeks after cells were injected. When the tumor reached this size, mice were euthanized. Grossly, the tumors formed expansile infiltrative masses that were adherent to and invading the musculature deep to the subcutis. The overlying skin was also adhered to the tumor. The tumors were firm, lobulated, reddish/maroon masses that bled readily on a cut surface.

The gross appearance of lungs from these animals was considered to be normal. In contrast, mice receiving an intravenous injection of SB-HSA cells through the tail vein and sacrificed after the injection were found to have multifocal maroon tumor nodules disseminated through the lungs as well as an occasional larger subcutaneous tumor.

Histopathological examination of tissue of these mouse tumors was indistinguishable from the canine hemangiosarcoma. The tumor tissue comprised clusters of small sheets of pleomorphic, elongated, plump spindle cells frequently forming slit-like spaces, many of which contained erythrocytes. The cells comprising these foci were polygonal to spindle shaped with small amounts of eosinophilic cytoplasm, usually indistinct cell margins, high nuclear to cytoplasmic ratios, with oval variably sized nuclei with finely stipled chromatin, and variably sized multiple nucleoli. There were 2 mitotic figures per high power field.

The angiogenic properties of the SB-HSA cell line of the present invention were also assessed using two in vivo assays.

In a corneal angiogenesis assay, also referred to herein as a corneal pocket angiogenesis assay, sponges containing SB-HSA cells implanted onto the avascular cornea of BALB/c mice induced marked neovascularization, with neovessels advancing from the limbus toward the sponge. Vessel ingrowth was detectable by two days following placement of the sponge with vessels reaching the sponge by 12 days. Control corneas receiving sponge implants but without SB-HSA cells did not show neovascularization.

In a subcutaneous MATRIGEL™/sponge assay in BALB/c mice, vascular invasion of the MATRIGEL™ plug arising from the periphery and progressing centrally towards the sponge was detectable after one week. By two weeks, there was marked arborization of the infiltrating blood vessels that formed a network surrounding the sponge containing the SB-HSA cells. Control MATRIGEL™/sponge implants lacking these tumor cells failed to elicit a vascular response.

Thus, in vivo, the cell line of the present invention stimulates a robust angiogenic response in mice and forms tumor masses composed of aberrant vascular channels in immunocompromised mice providing excellent opportunities for investigating the effectiveness of antiangiogenic agents.

For example, the corneal pocket angiogenesis assay was used to demonstrate the ability of Interleukin-12 (IL-12) to suppress angiogenesis induced by SB-HSA cells. IL-12 is a cytokine with both immunostimulatory and antiangiogenic effects. In these experiments, sponges containing 70,000 SB-HSA cells were placed into the corneas of BALB/c mice. Two days after placement of the sponges, the mice were randomized to receive either mrIL-12 or phosphate buffered saline. Each was delivered as a continuous subcutaneous infusion by subcutaneously implanted osmotic pumps. One week after treatment, mice were injected with FITC-dextran, euthanized and the corneas examined. IL-12-treated mice showed significantly less corneal neovascularity as compared to the PBS-treated control group.

Subcutaneous injection of the immortalized cell line of the present invention over the dorsum of immunocompromised mice was found to result in more rapid development of endothelial cell tumors as compared to other known immortalized endothelial cell lines. This rapid tumor growth provides a simple and quick means for evaluating the antiangiogenic affects of test agents through repeated measures of tumor size.

Accordingly, another aspect of the present invention relates to a mouse model for angiogenesis. The mouse model of the present invention comprises an immunocompromised mouse injected with the malignant endothelial cell line derived from canine hemangiosarcoma.

As demonstrated herein, tail vein injection of the cells provides a reliable and quick route to establish pulmonary metastasis following injection of SB-HSA cells in mice. Thus, one embodiment of the present invention relates to a mouse model comprising mice administered SB-HSA cells via tail vein injection. These mice serve as a useful model for screening potential antiangiogenic agents. A reduction in the number and/or size of pulmonary metastases in these mice following treatment with a potential antiangiogenic agent is indicative of the agent having antiangiogenic activity.

In another embodiment, the mouse is injected subcutaneously with cells of the cell line in its dorsum. Using this model, the effects of a test agent on angiogenesis can be assessed simply by measuring tumor growth or shrinkage of subcutaneous tumors in these mice. Further, this system for evaluating test agents for their ability to suppress angiogenesis allows repeated measures to be made in the same animal in a short time frame.

For example, IL-12 was also shown, to suppress the growth of canine hemangiosarcoma in vivo in this model. IL-12 is a cytokine with pleotropic effects including suppression of angiogenesis due to in vivo inhibition of endothelial cell growth. This activity is mediated by downstream chemokines such as IP-10 and Mig, which are induced by interferon-γ in response to IL-12. Accordingly, the capacity of IL-12 to suppress growth of SB-HSA tumors in the mouse model of the present invention was evaluated to demonstrate the usefulness of measuring inhibition of SB-HSA tumor development in this model in identifying agents that suppress endothelial cell growth and angiogenesis. Control mice that were injected subcutaneously with SB-HSA cells and received phosphate buffered saline developed tumors at the site of cell inoculation by the second week that progressively enlarged over a 4-week observation period. In contrast, the growth of tumors in the mice that received continuous subcutaneous infusions of IL-12 was initially suppressed for two weeks followed by slower growth and significantly smaller size by the end of the 4-week observation period.

Taken together, these experiments demonstrate the value of the mouse model of the present invention in investigating angiogenesis and identifying test agents with antiangiogenic activity. Test agents can be administered to mice injected with the SB-HSA cells in various formulations and using dosing regimes mimicking those expected to be used therapeutically for the agent. The ability of these agents to suppress angiogenesis can be assessed by monitoring tumor growth in these mice. Test agents that inhibit tumor growth in these mice possess antiangiogenic activity. For purposes of this invention, by "inhibit" it is meant that the test agent prevents the tumors in treated mice from increasing in size, decreases the rate at which tumors grow and/or decreases the size of the tumors as compared to untreated mice.

Agents identified as possessing antiangiogenic activity using the endothelial cell and/or murine models of the present invention are expected to be useful in inhibiting angiogenesis. Accordingly, such agents can be used in the treatment of cancer as well as other diseases and/or conditions mediated by uncontrolled angiogenesis.

As will be understood by those of skill in the art upon reading this disclosure, in addition to the exemplary mouse models described in detail herein, SB-HSA cells of the present invention may be injected in accordance with the teachings herein into other immunocompromised nonhuman mammals as well to produce additional animal models. In a preferred embodiment, the other immunocompromised nonhuman mammal is also a rodent such as an immunocompromised rat.

The following nonlimiting examples are provided to further illustrate the present invention.

EXAMPLES

Example 1

Source of Malignant Endothelial Cells

A nine-year-old German Shepherd dog was euthanized for an enlarging 20 cm fluctuant subcutaneous mass over the left shoulder. The mass had previously been biopsied and diagnosed as a hemangiosarcoma, a malignancy of endothelial cells, by a board certified veterinary pathologist. Immediately following euthanasia, a small piece of tumor was excised and used as the source of tissue to develop the current studies.

Example 2

Mice

Strains of mice used in these studies included BALB/c, bg/nu/XID, and NOD-SCID. All animals were initially purchased from Sprague-Harley, Indianapolis, Ind. and BALB/c and NOD-SCID mice were bred in a colony in house. The bg/nu/XID mice were used in experiments following receipt from the vendor. Mice were typically 8–12 weeks old when used in experiments.

Example 3

Development of SB-HSA Malignant Endothelial Cell Line

Several small pieces (<0.5 cm diameter) of the hemangiosarcoma biopsy were engrafted subcutaneously in the dorsal cervical area of a bg/nu/XID mouse. Prior to implantation, the tumor was washed in phosphate buffered saline (PBS) and gross blood clots or necrotic-appearing areas removed. The mouse was anesthetized with intraperitoneal injection of AVERTIN (tribromoethanol/tertiary amyl alcohol (1:1) diluted in 10% ethyl alcohol, 0.1 ml/10 grams of body weight). The fur was clipped and the skin cleansed with 70% ethanol. A small skin incision was made and a small subcutaneous pocket was created by blunt dissection. Tumor pieces were introduced into the pocket and the skin wound was sutured closed. Following recovery, the mouse was monitored for 120 days, at which time, a 1 cm diameter tumor was present and the animal was sacrificed. The tumor was excised and a portion was snap frozen with liquid nitrogen in O.C.T.™ (optimal cutting temperature) compound (TissueTek; Sakura Finetek USA, Torrance, Calif.) for immunohistochemical staining and the remainder was used for establishing the primary canine hemangiosarcoma cell line. The tumor tissue was minced and transferred to an Erlenmeyer flask containing a modified enzyme dissociation solution and glass beads, as described by Kemmner et al. (J. Cancer Res. Clin. Oncol. 1987 113:400–401). The enzyme dissociation solution consisted of type I collagenase 270 U/ml (Invitrogen Life Technologies, Baltimore, Md.), DNAse from bovine pancreas 200 U/ml (Sigma, Indianapolis, Ind.) and penicillin-streptomycin (10,000 IU/ml Penicillin, 10 mg/ml streptomycin) solution 1% v/v (Mediatech, Inc, Cellgro, Herndon Va.) dissolved in MEM Eagle with Earle's balanced salt solution (BioWhittaker, Walkersville, Md.). Tissue pieces were incubated at 37° C. in a 5% humidified $CO_2$ atmosphere with gentle agitation using a magnetic stirrer. After approximately one hour the suspension was allowed to stand for a few minutes in order for the larger undissociated pieces to settle. The top suspension was collected and passed through a 40 μm nylon mesh cell strainer, and centrifuged at 400×g for 8 to 10 minutes. The cell pellet was washed with PBS and centrifuged at 400×g for 8 to 10 minutes. Red blood cells were lysed with an ammonium chloride lysing buffer and the wash step was repeated. The cell pellet was resuspended in RPMI-1640 medium supplemented with 10% heat inactivated FBS, 1% v/v penicillin-streptomycin solution (BioWhittaker, Walkersville, Md.), 2 mM sodium pyruvate, 2 mM L-glutamine and 10 mM HEPES buffer (Sigma, Indianapolis, Ind.), transferred to a 75 $cm^2$ tissue culture flask, and incubated overnight at 37° C. in a humidified 5% $CO_2$ atmosphere. At that time, the medium was aspirated and the adherent cells were gently washed with PBS before EGM-2 endothelial cell medium (Bio Whittaker) was added back to the flask. The cells were expanded in EGM-2 medium and passaged when confluent.

After 14 passages the cells were sorted by direct two color immunofluorescence labeling. The brightest 10% of the cells labeling positive for expression of $\alpha_v\beta_3$ integrin and CD146 were collected, cultured in EGM-2 medium, and expanded. When sufficient cell numbers were available, $5\times10^6$ cells were injected subcutaneously into the dorsum of a bg/nu/XID) mouse and allowed to grow for 30 days until a 1 $cm^3$ tumor developed. The mouse was euthanized and the tumor was excised. Once again, a portion was snap frozen in O.C.T. compound for immunohistochemical staining and the remaining tumor was used to establish a single cell suspension using the method described above. This single cell suspension was then sorted a second time for bright staining with P1H12 and LM609. The brightest cells were collected and plated in 75 $cm^2$ flasks in EGM-2 medium for expansion. These cells, referred to herein as the SB-HSA cell line, developed from the second passage in a bg/nu/XID mouse, were used for the remainder of the experiments. The cells stained brightly for dual expression of $\alpha_v\beta_3$ integrin and CD146. Aliquots of early passages were frozen in liquid nitrogen.

Example 4

Flow Cytometry

Cell sorting and flow cytometric analysis of the SB-HSA cell line were done by direct two color immunofluorescence labeling using a FACSCalibur cell sorter or a FACScan flow cytometer (Becton Dickinson, San Jose, Calif.). For cell sorting and flow cytometry, fluorescein isothiocyanate (FITC)- or phycoerythrin(PE)-conjugated monoclonal antibodies (mAbs) specific for two endothelial cell surface antigens were used. Murine mAb P1H12 (IgG1, Chemicon Int, Temecula, Calif.), which recognizes CD146, an endothelial surface antigen (Solovey et al. N. Engl. J. Med. 1997 337:1584–1590), was conjugated to FITC, and mAb LM609 (IgG1, Chemicon), which recognizes $\alpha_v\beta_3$ integrin (CD51/CD61) in numerous species (except mouse) was conjugated to PE (Illera et al. Biol. Reprod. 2003 68:766–771; Sipkins et al. Nat. Med. 1998 4:623–626; Fox et al. Microvasc. Res. 2002 64:414-424; Frame et al. Microcirculation 2001 8:403–13; Bhattacharya et al. Am. J. Physiol. Lung Cell Mol. Physiol. 2001 280:L1049–1056; Leven and Tablin, Exp. Hematol. 1992 20:1316–1322; Miyauchi et al. J. Biol. Chem. 1991 266:20369–20374; and Cheresh, D. A. Proc. Natl. Acad. Sci. 1987 84:6471–6475).

SB-HSA cells were washed with HBSS and detached with 5 mM EDTA. Cells were then collected with EGM-2 medium and centrifuged at 400×g for 6 to 10 minutes. The cell pellet was washed with PBS depleted of Mg and Ca (dPBS) and centrifuged at 400×g for 6 to 10 minutes. The washed cells were resuspended in 1 ml of dPBS containing 1% BSA, adjusted to a concentration of $5\times10^6$/ml and 50 μl ($2.5\times10^5$ cells) were placed into microcentrifuge tubes for staining. Monoclonal antibodies (5 μg/ml final) were added to individual tubes and the cells were incubated at 4° C. in the dark for 30 minutes, then washed with cold dPBS containing 1% BSA. FITC- or PE-conjugated irrelevant mouse IgG1 antibodies (10 μl/$1\times10^6$ cells) were added to some tubes as isotype controls. Propidium iodide was added just before cell analysis as a live-dead discriminator. Ten thousand events were collected and analyzed with the CellQuest v.3.3 software package (Becton Dickinson). Additional antibodies used in flow cytometry experiments included rat antimouse c-kit (CD117, Pharmingen, San Diego, Calif.) conjugated to PE and an irrelevant rat antimouse IgG2b conjugated to PE as its control.

Example 5

SB-HSA Tumor Senograft

Canine hemangiosarcoma xenografts were established in NOD-SCID mice by injection of $5\times10^6$ SB-HSA cells suspended in 200 μl PBS over the dorsum using a 26 gauge needle and tuberculin syringe. Mice were examined every other day until tumors were detected and measured with calipers. Animals were sacrificed when tumors reached a size of 1 $cm^3$.

In some experiments, $5\times10^6$ SB-HSA cells were injected intravenously into the tail vein.

Example 6

Pathology

Gross and histopathological examination of tissues from experimental mice were performed. For histological examination, routine hematoxylin and eosin staining of fixed sections was done.

Example 7

Immunohistochemistry

Immunohistochemical staining was performed on fresh frozen and formalin-fixed paraffin embedded sections from SB-HSA tumors obtained from bg/nu/XID and NOD-SCID mice. Antibody clone P1H12 (anti-CD146, Chemicon) and LM609 (anti-$\alpha_v\beta_3$ integrin [CD51/CD61], Chemicon) were used on fresh frozen sections while PECAM-1 (anti-CD31, clone JC/70A, Dako, Carpinteria, Calif.) and anti-Factor VIII polyclonal antibody (von Willebrand☐s factor, Signet, Dedham, Mass.) were used on fixed tissue sections following antigen retrieval.

The final product was developed using alkaline phosphatase with New Fuchsin as the chromogen (Histo-Mark Red Kit, Kirkegaard & Perry Labs, Gaithersburg, Md.), as described by Ritt et al. (Cancer Lett 158:73–84, 2000) and Koenig et al. (Vet Pathol, 39, 458–472, 2002) Immunohistochemistry was performed by IHC Services (J. Wojcieszyn, Ph.D., Smithville, Tex.).

Example 8

Reverse Transcription-Polymerase Chain Reaction (RT-PCR)

Total RNA was extracted from SB-HSA cells with TRIzol reagent (Invitrogen Life Technologies (Gibco), Baltimore, Md.) and reverse transcription was performed using Super-Script™ First Strand Synthesis Systems for RT-PCR (Invitrogen Life Technologies) according to the manufacturer's instructions. The PCR products were electrophoresed on a 1% agarose gel, stained with ethidium bromide and visualized with UV light. Primers, $MgCl_2$ concentrations and conditions used to detect message of interest in endothelial cells markers as follows:

| CDNA | Primers* Forward: 5'-3' Reverse: 5'-3' | Thermal Cycler Program** | PCR Product (bp) |
|---|---|---|---|
| VEGF | CCA TGA ACT TTC TGC TCT CTT G (SEQ ID NO: 1) TTG TCT TGC TCT ATC TTT CTT (SEQ ID NO: 2) | 95° C. 1 min, 60° C. 1 min, 72° C. 1 min | 450 |
| VEGFR-1 (flt) | AAG CAG CCC ATT CAT GGT CTT TGC (SEQ ID NO: 3) CCA TCA GGG ATC AGG GTA TCA AG (SEQ ID NO: 4) | 95° C. 1 min, 58° C. 1 min, 72° C. 1 min, | 380 |
| VEGFR-2 (flk) | ACT GGA GCC TAC AAG TGC TTC TAY (SEQ ID NO: 5) TYT TCT TGG TCA TCA GYC CAC TG (SEQ ID NO: 6) | 95° C. 1 min, 59° C. 30 sec, 72° C. 1 min, | 650 |
| BFGF | CTT CAA GGA CCC CAG CGG C (SEQ ID NO: 7) GCT CTT AGC AGA CTT GG (SEQ ID NO: 8) | 94° C. 30 sec, 55° C. 30 sec, 72° C. 1 min, | 400 |
| IL-8 | TCA GAA CTT CGA TGC CAG (SEQ ID NO: 9) TTT CAC CGA TCT TGT TTC TC (SEQ ID NO: 10) | 94° C. 1 min, 52° C. 1 min, 72° C. 1 min, | 227 |
| MMP-2 | CC GTA TGA GAT CAA GCA GAT (SEQ ID NO: 11) TTA CGG GTC CTC AAT ATC GAG (SEQ ID NO: 12) | 94° C. 30 sec, 56° C. 30 sec, 72° C. 30 sec | 450 |
| MMP-13 | ATC TGT ATG AGG AAG ACT (SEQ ID NO: 13) GAC CAG AAG GTC CAT CAA (SEQ ID NO: 14) | 94° C. 30 sec, 53° C. 30 sec, 72° C. 30 sec | 450 |
| SCF | CCA GAG TCA GTG TCA CAA AAC C (SEQ ID NO: 15) CTT CTT CCA GTA TAA GGC TCC (SEQ ID NO: 16) | 94° C. 1 min, 58.5° C. 1 min, 72° C. 1 min | 196 |
| c-kit | CAC CCT GGT CAT TAC AGA ATA TTG (SEQ ID NO: 17) CGG AAG CCT TCC TTN ATC ATC TTG (SEQ ID NO: 18) | 95° C. 30 sec, 58° C. 30 sec, 72° C. 30 sec | 650 |

-continued

| CDNA | Primers*<br>Forward: 5'-3'<br>Reverse: 5'-3' | Thermal<br>Cycler<br>Program** | PCR<br>Product<br>(bp) |
|---|---|---|---|
| β-actin | CAT GTT TGA GAC ATT CAA CAC CCC<br>(SEQ ID NO: 19)<br>GCC ATC TCT TGC TCG AAG TCC AG<br>(SEQ ID NO: 20) | 95° C. 1 min,<br>50° C. 1 min,<br>72° C. 1 min | 325 |

*All primers were canine-specific sequences except β-actin, which was a human specific sequence
**Thirty-five cycles were used for all amplifications except β-actin cDNA that was amplified by 30 cycles. All conditions used a 95–96° C. 2-minute hot start with the exception of c-kit and β-actin. A final 7-minute extension at 72° C. was used for all reactions. The concentration of $MgCl_2$ was 1.5 mM in all reactions except VEGF, IL-8, and c-kit where it was 3 mM.

Example 9

Corneal Angiogenesis Assay

Polyvinyl sponges (Rippey, Eldorado Hills, Calif.) preirradiated with 2000 Gy of gamma irradiation (cesium source) were cut into 4×4×2 mm pieces, and 70,000 SB-HSA cells were introduced into the sponges. BALB/c mice were anesthetized with AVERTIN and a small surgical micropocket was created in the center of the avascular cornea. Sponges were then inserted into the micropocket. Eyes were examined for neovascularization daily using an ophthalmic microscope (Carl Zeiss Inc, Thornwood, N.Y.). On day 14 after implantation, 200 µl of FITC-conjugated high molecular weight dextran (2,500,000 MW, 200:1, Sigma) (FITC-dextran) was injected into the tail vein, and the animal was sacrificed 5 minutes later. The eyeball was enucleated from the orbital cavity and fixed for 5 minutes in 4% paraformaldehyde. The cornea with the adjacent limbus was dissected, rinsed in PBS, and mounted on a glass slide in 10% glycerol. Phase contrast and fluorescence microscopy were used to visualize the general layout of the cornea and the presence of perfused blood vessels, respectively (Muthukkaruppan, V. and Auerbach, R. Science 1979 205:1416–1418).

Example 10

Subcutaneous Matrigel/Sponge Assay

Matrigel (500 µl, 500:1, BD Biosciences, Bedford, Mass.) was injected subcutaneously with a 27 gauge needle in the flank region of 2.5–3.5 month old BALB/c mice and allowed to solidify for 30–60 minutes. At that time, mice were anesthetized with AVERTIN given intraperitoneally. The fur overlying the Matrigel plug was clipped, the skin cleansed with betadine, and a stab incision was made with a sterile #15 surgical blade over the Matrigel bleb. A stab incision was then made directly into the Matrigel plug. A sterilized polyvinyl sponge (3×2×1.5 mm) containing $1 \times 10^5$ SB-HSA tumor cells was introduced through the nick in the Matrigel and advanced to the center of the plug with a thumb forceps.

The skin wound was closed with a 6-0 nylon suture and the mouse recovered under a heat lamp. Mice were observed after 24 hours to monitor condition of the wound.

After two weeks, 200 µl of FITC-dextran was injected through the tail vein. Mice were euthanized 3–5 minutes later; the Matrigel plug was removed, separated from the abdominal muscle and fixed in 10% formalin. Phase contrast microscopy was used to examine the topography of the Matrigel plug, and the perfused blood vessels were visualized using fluorescence illumination.

Example 11

Treatment of SB-HSA Tumor-Bearing Mice with IL-12

NOD-SCID mice were injected subcutaneously over the dorsum with SB-HSA cells ($5 \times 10^6$ cells/200 µl). Two days later, they were anesthetized by intraperitoneal injection of AVERTIN and osmotic pumps (Alzet Corporation, Palo Alto, Calif.) containing 33.3 µg in 200 µl of murine recombinant (mr) IL-12 (Peprotech, Rocky Hill, N.J.) or 200 µl of PBS were inserted subcutaneously through a small skin incision. The skin wound was closed with wound clips. Pumps were designed to deliver 6 µl/day (1 µg IL-12/day for four weeks. The mice were examined every other day for tumor development. The two largest perpendicular diameters were measured with calipers.

What is claimed is:

1. An immortalized hemangiosarcoma cell line comprising immortalized malignant canine endothelial cells, said immortalized malignant canine endothelial cells expressing CD146, $\alpha_v\beta_3$ integrin, PECAM-1, and Factor VIII and causing canine hemangiosarcoma when injected into an immunocompromised rodent.

2. The immortalized cell line of claim 1 wherein the immortalized malignant canine endothelial cells are isolated from a tumor grown in a mouse transplanted with canine hemangiosarcoma cells.

3. An endothelial cell model for angiogenesis comprising the immortalized cell line of claim 1.

4. An immortalized hemangiosarcoma cell line comprising cells of ATCC Deposit Number PTA6071, said cells causing canine hemangiosarcoma when injected into an immunocompromised rodent.

* * * * *